United States Patent [19]

Jupe et al.

[11] 4,324,925

[45] Apr. 13, 1982

[54] PROCESS FOR THE PREPARATION OF POLYHYDRIC PHENOLS

[75] Inventors: Christoph Jupe, Cologne; Helmut Waldmann, Leverkusen; Hermann Seifert, Cologne, all of Fed. Rep. of Germany

[73] Assignee: Bayer Aktiengesellschaft, Leverkusen, Fed. Rep. of Germany

[21] Appl. No.: 164,444

[22] Filed: Jun. 30, 1980

[30] Foreign Application Priority Data

Jul. 17, 1979 [DE] Fed. Rep. of Germany ....... 2928743

[51] Int. Cl.$^3$ .................. C07C 39/12; C07C 79/24; C07C 91/30; C07C 149/36
[52] U.S. Cl. .................................. 568/719; 568/712; 568/717; 568/721; 568/731; 568/735; 568/737; 568/741; 568/743; 568/771; 568/767; 568/650; 560/70; 560/86; 562/464; 562/478
[58] Field of Search ............... 568/763, 719, 741, 771, 568/721, 798, 803, 749, 774, 758, 717, 743, 650, 735, 734, 767; 560/745, 86, 70; 562/468, 478; 768/748, 749

[56] References Cited

U.S. PATENT DOCUMENTS

| 2,734,925 | 2/1956 | Neuworth | 568/758 |
| 2,785,206 | 3/1957 | Neuworth | 568/758 |
| 4,208,536 | 6/1980 | Constantini et al. | 568/771 |
| 4,214,105 | 7/1980 | Seifert et al. | 568/771 |

FOREIGN PATENT DOCUMENTS

| 1239701 | 5/1967 | Fed. Rep. of Germany | 568/758 |
| 1668952 | 11/1969 | Fed. Rep. of Germany . | |
| 1231991 | 5/1971 | United Kingdom | 568/754 |

OTHER PUBLICATIONS

Kirth-Othmer, "Encyclopaedia of Chem. Techn.," 2nd ed., vol. 11, pp. 462 to 492 esp. pp. 469 & 488 (1966).

*Primary Examiner*—Werren B. Lone
*Attorney, Agent, or Firm*—Sprung, Felfe, Horn, Lynch & Kramer

[57] ABSTRACT

An improved process for the preparation of a polyhydric phenol by hydroxylation of a phenol with a peroxidic hydroxylating agent, is disclosed. The improvement resides in that before the hydroxylation, all or some of the mixture to be hydroxylated is treated with a cation exchanger.

15 Claims, No Drawings

PROCESS FOR THE PREPARATION OF POLYHYDRIC PHENOLS

The present invention relates to an improved process for the preparation of polyhydric phenols by hydroxylation of phenols.

When phenols are hydroxylated, one or more hydroxyl groups are introduced into phenols, aromatic compounds which have two or more hydroxyl groups bonded directly to one or more aromatic nuclei (=polyhydric phenols) being formed. The most important polyhydric phenols are those which have two hydroxyl groups on one aromatic nucleus and are derived from phenol, naphthalene, anthracene and phenanthrene. These dihydric phenols are industrially important compounds which are prepared in large amounts and are used, for example, in the field of photography, of dyestuffs and plastics and of aroma substances and flavour substances, and in particular as intermediate products in these fields (see, for example, Kirk-Othmer, Encyclopaedia of Chemical Technology, Second Edition, Volume 11, pages 462 to 492, in particular pages 469 and 488 (1966)).

A number of processes for the preparation of polyhydric phenols in which polyhydric phenols are obtained by hydroxylation of phenols are known. Peroxidic compounds, for example hydrogen peroxide, peroxo salts or peracids, in particular percarboxylic acids, are frequently used as the hydroxylating agent (see, for example, DE-AS (German Published Specification) No. 2,064,497, DE-AS (German Published Specification) No. 1,593,968, DE-AS (German Published Specification) No. 1,543,830, DE-AS (German Published Specification) No. 2,364,181, DE-AS (German Published Specification) No. 2,407,398, DE-OS (German Published Specification) No. 2,658,866 and DE-OS (German Published Specification) No. 2,658,943).

In general, the phenols to be hydroxylated are employed in a large excess, relative to the peroxidic hydroxylating agent, in these processes, that is to say the phenols to be hydroxylated are only partly hydroxylated. Thus, for example, DE-OS (German Published Specification) No. 1,593,968 states that the degree of conversion of the phenol employed should not exceed 30%, since otherwise the yield of polyhydric phenols, in this case diphenols, decreases very rapidly. DE-OS (German Published Specification) No. 2,364,181 states that if peracids are used as hydroxylating agents for phenols, it is expedient to employ not more than 0.5 mol of peracid per mol of phenol, since larger amounts of this oxidizing agent effect secondary oxidation which decreases by an extreme extent the yield of the desired product.

When such processes are carried out industrially, the unreacted portions of the phenols employed are therefore recovered after the hydroxylation reaction and re-used in that reaction. If appropriate, fresh phenols are added to the recycled phenols in an amount corresponding to that which has been reacted in the hydroxylation reaction.

It has now been established that the selectivity of the formation of polyhydric phenols is not satisfactory either when fresh phenols exclusively are used or, in particular, when recycled phenols are used.

A process has now been found for the preparation of polyhydric phenols by hydroxylation of phenols with peroxidic hydroxylating agents, which is characterized in that, before the hydroxylation, all or some of the phenol to be hydroxylated is treated with a cation exchanger. The ion exchanger can be one which also contains basic groups.

Examples of possible ion exchangers for the process according to the invention are liquid or solid ion exchangers which contain acid and, if appropriate, also basic groups. In particular, such ion exchangers which are built up from organic or inorganic polymers can be used. The ion exchangers can be built up, for example, from organic resins based on vinylbenzene, divinylbenzene, vinyl alcohol, (meth)acrylic acid, ethylene or perfluoroethylene or copolymers thereof. The ion exchangers can also be built up from organic polymers based on one or more of the abovementioned substances in combination with other polymerizable substances, for example in combination with styrene. Suitable inorganic ion exchangers are, for example, those based on silicate.

Ion exchangers which can be employed according to the invention contain, for example, $SO_3^-$ and/or $COO^-$ groups, as functional groups. They can additionally contain basic groups, for example $NH_2$, NH-alkyl, N-dialkyl, N-alkyl-hydroxyalkyl and/or N-diaryl groups, as functional groups. The functional groups can be in the acid respectively basic form or completely or partly in salt form.

It is also possible to use several of the above-mentioned ion exchangers successively in any desired sequence, or in the form of any desired mixture.

Ion exchangers having the abovementioned characteristics are commercially available.

Ion exchangers which are built up from a base polymer (matrix) of styrene/divinylbenzene, styrene/acrylic acid, divinylbenzene/acrylic acid, styrene/methacrylic acid or divinylbenzene/methacrylic acid and which contain $HSO_3$ and/or HOOC groups as functional groups are preferably employed in the process according to the invention. They can optionally contain $N(CH_3)_2$, $N(CH_3)(CH_2-CH_2-OH)$ and/or $N^{\oplus}(CH_3)_2(CH_2-CH_2-OH)$ groups as additional functional groups. The functional groups can also be present in the free form or completely or partly in salt form in the case of the ion exchangers which are preferably to be employed. An exchanger resin which contains aminocarboxylic acid radicals as functional groups is likewise particularly suitable for the process according to the invention.

Solid ion exchangers based on acrylic acid/divinylbenzene are particularly preferably employed, the HOOC groups being present in the free form or completely or partly in the form of their metal salts, in particular their alkaline earth metal salts and/or alkali metal salts.

The phenols to be hydroxylated, all or some of which are treated, according to the invention, with ion exchangers before the hydroxylation reaction, are the most diverse aromatic compounds which contain one or more hydroxyl groups bonded to one or more aromatic nuclei and into which one or more hydroxyl groups can be introduced by means of peroxidic hydroxylating agents. These compounds are called phenols in the following text.

It is possible for the phenols to contain no other substituents besides one or more hydroxyl groups, but they can also carry different substituents if these do not impede the hydroxylation reaction. Possible phenols are, for example, aromatic hydroxy compounds which are derived from benzene, naphthalene, phenanthrene or anthracene and which still contain at least one free hydrogen atom on an aromatic nucleus. In the case of phenols which are derived from benzene, there is preferably a free hydrogen atom in the 2-position or 4-position relative to a hydroxyl group which is already present. In addition to one or more hydroxyl groups on the aromatic nucleus or nuclei, the phenols can contain, for example, one or more identical or different aliphatic, cycloaliphatic, phenyl or naphthyl radicals as substituents. Examples of possible aliphatic radicals are straight-chain and branched radicals with, for example, 1 to 10 C atoms, such as methyl, ethyl, isopropyl, n-butyl, i-butyl, tert.-butyl, n-pentyl, 2-methylbutyl, 3-methylbutyl, 2-ethylpropyl, n-hexyl, 2-methylpentyl, 3-methylpentyl, 4-methylpentyl, n-heptyl, n-octyl, 2-ethylhexyl, n-nonyl, 2-ethylheptyl and n-decyl. Examples of possible cycloaliphatic radicals are those with 3 to 12 C atoms, such as cyclopropyl, cyclobutyl, cyclopentyl, cyclohexyl, cycloheptyl, cyclooctyl, cyclononyl and cyclodecyl.

In the aliphatic, cycloaliphatic, phenyl and naphthyl radicals, in each case one or more hydrogen atoms can be replaced by groups which are stable under the conditions of the hydroxylation reaction. Examples of such groups are one or more fluorine, chlorine and/or bromine atoms; and one or more $C_1$- to $C_5$-alkoxy, $C_1$- to $C_5$-dialkylamino, carboxyl, nitro, cyano and/or sulphonic acid groups and/or carbalkoxy groups, the alkoxy radicals of which have 1 to 10 C atoms.

The aromatic nucleus or nuclei of the phenols can also be substituted by one or more of these atoms or groups.

Phenols which are derived from benzene are preferably used in the process according to the invention.

For example, phenols of the formula

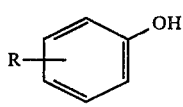 (I)

wherein
R represents hydrogen, $C_1$- to $C_{10}$-alkyl, $C_3$- to $C_{12}$-cycloalkyl, phenyl, naphthyl, fluorine, chlorine, bromine or a nitro, cyano, sulphonic acid, carboxyl, carbo-$C_1$- to $C_{10}$-alkoxy, $C_1$- to $C_3$-alkoxy or $C_1$- to $C_4$-dialkylamino group, it being possible for the alkyl and cycloalkyl radicals to be substituted by fluorine, chlorine or bromine atoms or $C_1$- to $C_5$-alkoxy, $C_1$- to $C_4$-dialkylamino, carboxyl, nitro, cyano, sulphonic acid or $C_1$- to $C_{10}$-carbalkoxy groups and for the phenyl and naphthyl radicals to be substituted by fluorine, chlorine, bromine, $C_1$- to $C_{10}$-alkyl, $C_3$- to $C_{12}$-cycloalkyl or nitro, carboxyl, carbo-$C_1$- to $C_{10}$-alkoxy, $C_1$- to $C_5$-alkoxy, cyano, sulphonic acid or $C_1$- to $C_4$-dialkylamino groups, can be employed in the process according to the invention.

A preferred group of phenols within the formula (I) corresponds to the phenols of the formula

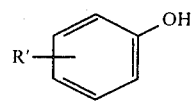 (II)

wherein
R′ represents hydrogen, $C_1$- to $C_3$-alkyl, $C_5$- to $C_7$-cycloalkyl, phenyl, fluorine, chlorine or a nitro, sulphonic acid, carbohydroxy, carbo-$C_1$- to $C_3$-alkoxy, $C_1$- to $C_2$-alkoxy or $C_1$- to $C_2$-dialkylamino group.

Monohydric phenols of the formula

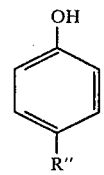 (III)

wherein
R″ denotes for hydrogen, $C_1$- to $C_5$-alkyl, $C_5$- to $C_7$-cycloalkyl, phenyl, fluorine, chlorine or a nitro, sulphonic acid, carbohydroxy, carbo-$C_1$- to $C_3$-alkoxy, $C_1$- to $C_3$-alkoxy or $C_1$- to $C_2$-dialkylamino group,
are particularly preferably employed in the process according to the invention.

Specific examples which may be mentioned of phenols which are suitable for use in the process according to the invention are: phenol, o-cresol, m-cresol, p-cresol, p-cyclohexylphenol, o-cyclohexylphenol, p-phenylphenol, o-phenylphenol, m-phenylphenol, p-ethylphenol, o-ethylphenol, m-ethylphenol, o-isopropylphenol, p-isopropylphenol, o- or p-tert.-butylphenol, p-nitrophenol, o-nitrophenol, m-nitrophenol, 2-bromo-4-methylphenol, p-chlorophenol, o-chlorophenol, m-chlorophenol, p-carbomethoxyphenol, salicylic acid ethyl ester, p-cyclopentylphenol, o-dimethylaminophenol, p-cyano-phenyl, p-methoxy-phenol, o-isopropoxyphenol, p-ethoxy-phenol, 3,5-diethyl-phenol, thymol, phenol, carvaorol, 1,2,3-xylenol, 1,2,4-xylenol, 1,3,2-xylenol, 1,3,4-xylenol, 1,3,5-xylenol, 1,4,2-xylenol, α-naphthol, β-naphthol, 1-hydroxy-4-methylnaphthalene, 1-hydroxy-2-methylnaphthalene, 2-hydroxy-1-methylnaphthalene, 2-hydroxy-6-methylnaphthalene, 1-hydroxy-4-isopropylnaphthalene, 1-hydroxy-4-t-butylnaphthalene, 1-hydroxy-6-phenyl-naphthalene, 1-hydroxy-6-methoxy-naphthalene, 1-hydroxy-anthracene and 2-hydroxy-anthracene.

Phenol ($C_6H_5OH$) is very particularly preferably employed in the process according to the invention.

The process according to the invention can be applied to phenols which are to be hydroxylated and have not been reacted in the hydroxylation reaction and have been separated off and are recycled into the hydroxylation reaction (called recycled phenols in the following text), and to fresh phenols which are employed in the hydroxylation reaction (called fresh phenols in the following test). In general, it is advantageous to combine the total amount of recycled phenols and fresh phenols, to subject them to the process according to the invention together and then to pass them to the hydroxylation reaction together. However, it is also possible to subject the total amount of recycled phenols and the total amount of fresh phenols separately to the process according to the invention and then to pass them, together or separately, to the hydroxylation reaction. In certain cases, good results are also achieved if only the recycled phenols or only the fresh phenols are subjected to the process according to the invention. It is also possible, in certain cases, to subject only a part of the recycled phenols and/or of the fresh phenols or a part of the mixture of recycled phenols and fresh phenols to the process according to the invention.

If it is not intended to subject all the fresh phenols and recycled phenols to the process according to the invention, it is in general advantageous to established by preliminary experiments, if appropriate on a reduced scale, what proportion of fresh and/or recycled phenols can be excluded from the treatment in the process according to the invention without lowering the selectivity of the formation of hydroxylated phenols too greatly. In many cases it is not possible to establish this by analytical investigations of the phenols.

In carrying out the process according to the invention, a procedure is in general followed in which the phenols to be subjected to the treatment are treated in the liquid form with the ion exchanger or exchangers. For this, either molten phenols or dissolved phenols can be brought into contact with the ion exchanger or exchangers. The phenols are advantageously brought into contact with the ion exchangers in the dissolved form if they have melting points above 120° C. and if the desired treatment temperature is below their melting point. Possible solvents for the phenols are, in principle, all solvents which are sufficiently inert and which have an adequate dissolving power for the phenols. The solvents preferably used are those which are also employed in the hydroxylation reaction. For example, water can be used as the solvent if the phenols are to be hydroxylated with an aqueous solution of $H_2O_2$, or organic solvents, such as benzene, chlorinated hydrocarbons or carboxylic acid esters, can be used if the hydroxylation is to be carried out with percarboxylic acids which are dissolved in benzene, chlorinated hydrocarbons or carboxylic acid esters.

The treatment, according to the invention, with ion exchangers can be carried out at various temperatures. In general, it can be carried out at temperatures in the range from 0° to 200° C. The treatment is preferably carried out at temperatures in the range from 20° to 120° C., and particularly preferably in the range from 40° to 100° C. In all cases, it should be ensured that the treatment temperature is not above that temperature at which the ion exchanger or exchangers used start to become unstable.

The process according to the invention can be carried out by a technological procedure which is in itself known. For example, all the procedures which are usually applied when the ion exchangers described are employed are suitable. Thus, solid ion exchangers in the form of granules or in any desired particle form are stirred into the molten or dissolved phenols, and are separated off mechanically after the treatment. The procedures known as fixed bed processes, fluidized bed processes or suspended bed processes are preferably used, and the fixed bed process in which the molten or dissolved phenols flow over a solid ion exchanger in a column is particularly preferred.

The period of treatment in the process according to the invention can vary within wide limits. In general, treatment times in the range from 1 to 300 minutes are adequate. The treatment time is preferably 5 to 180 minutes, and particularly preferably 10 to 120 minutes.

Since the phenols are in general sensitive towards oxygen, it is generally advantageous to exclude air or oxygen before, during and after the treatment according to the invention, for example by blanketing the mixture with an inert gas, such as nitrogen.

The ratio between the amounts of ion exchanger and phenols can also vary within wide limits. In the case of a discontinuous procedure, for example, 1 part by weight of cation exchanger can be used for the treatment of 1 to 1,000 parts by weight of phenols. The utilization of the ion exchanger can also be increased considerably by using it several times.

If a continuous procedure is followed, for example by allowing molten or dissolved phenols to flow over a stationary ion exchanger, the amount of ion exchanger and the flow rate can be chosen, for example, such that one part by weight of ion exchanger is brought into contact with 0.1 to 1,000 parts by weight of phenols per hour. 1 part by weight of ion exchanger is brought into contact with preferably 0.5 to 300, and particularly preferably with 1 to 20, parts by weight of phenols per hour.

In general, the ion exchangers can be used several times in the case of a discontinuous procedure, or for a prolonged period in the case of a continuous procedure. For example, a total of up to $10^8$ parts by weight of phenols can be treated with 1 part by weight of ion exchanger.

Ion exchangers used in the process according to the invention can be regenerated in a manner which is in itself known by the customary treatment with water, acid and/or alkali and can then be used again in the process according to the invention.

The process according to the invention is advantageously used in the hydroxylation of phenols with peroxidic hydroxylating agents. Such peroxidic hydroxylating agents are compounds which contain one or more —O—O— groups, for example $H_2O_2$, peroxodisulphates, Caro's acid, alkyl or aryl hydroperoxides, diacyl peroxides, percarboxylic acids, percarbonates, perborates and adducts of $H_2O_2$, for example the urea adduct of $H_2O_2$.

The process according to the invention can be used, for example, in the following known hydroxylations of phenols:

In the hydroxylation of phenol, substituted phenols or phenol derivatives with hydrogen peroxide in the presence of catalytic amounts of a strong acid (see DE-AS (German Published Specification) No. 2,064,497).

In the hydroxylation of aromatic compounds with hydrogen peroxide in hydrofluoric acid as the reaction medium (see DE-OS (German Published Specification) No. 1,543,953).

In the preparation of pyrocatechol and hydroquinone by hydroxylation of phenol with hydrogen peroxide in an aqueous medium, under catalysis by pseudo-aromatic iron-II compounds (see DE-OS (German Published Specification) No. 2,407,398).

The process according to the invention is preferably used in the following hydroxylation:

In the preparation of polyhydric phenols by hydroxylation of phenol with a solution, which is largely anhydrous and free from hydrogen peroxide, of a percarboxylic acid in an organic solvent (see DE-OS (German Published Specification) No. 2,658,943). The percarboxylic acid preferably contains 1 to 4 C atoms and the organic solvent is, for example, benzene, 1,2-dichloropropane or ethyl acetate.

A possible industrial embodiment of the process according to the invention can be carried out as follows:

The phenol originating from the working up of phenol which has already been hydroxylated is passed continuously, at 50° to 90° C., over an acid ion exchanger based on a sulphonated styrene/divinylbenzene copolymer or on an acrylic acid resin at a rate such that the average residence time is 5 to 60 minutes. The amount of phenol consumed by reaction is added to this stream of phenol before or after the treatment with the ion exchanger. The feed phenol mixture thus obtained is passed continuously to an arrangement of reaction vessels into which, in addition to the phenol mixture, a solution of a percarboxylic acid with 1 to 4 C atoms in an inert organic solvent, such as 1,2-dichloropropane, benzene or ethyl acetate, is simultaneously added continuously. When the reaction of the percarboxylic acid has ended, the reaction mixture, which consists predominantly of phenol, the organic solvent, the corresponding carboxylic acid with 1 to 4 C atoms and the reaction products pyrocatechol and hydroquinone, is passed to a distillative working up operation, in which, inter alia, the unreacted phenol is recovered.

The process according to the invention has the advantage that it can be carried out in a simple manner without particular expenditure on apparatus, avoids expensive separation and purification operations and requires, as auxiliaries, only ion exchangers, which have long service lives and can be regenerated. When the process according to the invention is applied, hydroxylated phenols are obtained in a higher selectivity than in the case of known processes, that is to say, for comparable conversions of phenols, hydroxylated phenols are obtained in a higher yield.

It is to be regarded as decidedly surprising that, with the treatment, according to the invention, with ion exchangers, it is possible to obtain phenols which can be converted into hydroxylated phenols, by hydroxylation with peroxidic hydroxylating agents, with a higher selectivity than phenols which have not been treated according to the invention.

It is indeed known that the content of certain impurities from crude phenol, containing impurities which can interfere with the preparation of secondary products of the phenol, can be lowered by treating the crude phenol with certain ion exchangers under certain conditions and then subjecting the phenol thus treated to distillation (see DE-OS (German Published Specification) No. 1,668,952). However, in this known procedure, the treatment with ion exchangers does not remove troublesome impurities. Impurities which cannot be removed by distillation (for example mesityl oxide) are converted, under the catalytic influence of the ion exchangers, into products (for example into higher condensation products) which can be separated off from phenol by distillation. Distillation is always necessary to separate off the troublesome impurities or their secondary products. Furthermore, in this known process, it is in general necessary also to carry out a treatment with acids and a neutralisation in order to obtain good results, that is to say a phenol which is as pure as possible.

According to the present invention, in contrast, phenols are only treated with ion exchangers. Subsequent distillation and additional treatment with acids and neutralisation are not necessary. On the basis of the statements in DE-OS (German Published Specification) No. 1,668,952, it could not be expected that solely the treatment of phenols with ion exchangers produces better phenols which can advantageously be used in the hydroxylation with peroxidic hydroxylating agents.

EXAMPLES

Example 1

As described below in detail, phenol ($C_6H_5OH$) was reacted with less than the equivalent amount of perpropionic acid and the reaction mixture obtained was worked up by distillation. After separating off components of high and low volatility, the unreacted phenol was taken off as the liquid product from a rectification column and passed to a treatment with an ion exchanger.

For this treatment, the phenol which had been separated off was pumped upwards, at a throughput rate of 9 kg per hour, through a vertical high-grade steel column (diameter 100 mm, height 500 mm), which was kept at an internal temperature of 60° C. by means of a heating jacket. The column was packed with 1.74 kg of a macroporous, weakly acid ion exchanger of the acrylic acid type, which had been washed with phenol beforehand (calculated as the dry substance).

The product issuing from the column was collected in a collecting vessel and kept as a melt at 60° to 70° C. under a blanket of nitrogen.

20 kg of fresh phenol (commercial material) were added to 160 kg of this phenol and, after thorough mixing, the phenol mixture thus obtained was used as the feed phenol for the reaction described below.

The prepared phenol was fed, at a throughput rate of 11 kg per hour, to the first reaction vessel of a 4-stage stirred cascade of kettles, 2.3 kg per hour of a solution of perpropionic acid in benzene/propionic acid simultaneously being introduced into this vessel. The perpropionic acid solution contained 19.5% by weight of perpropionic acid, 13.3% by weight of propionic acid and 67% by weight of benzene. The reaction vessels each had a useful volume of 1.7 l and were kept at an internal temperature of 42° C. The reaction mixture was forced once through all the 4 reaction vessels by the blanket of nitrogen in the first reaction vessel and by the product stream.

Downstream of the 4th reaction vessel, a content of 0.04% by weight of perpropionic acid was determined in the reaction mixture, which corresponds to a conversion of 99% of the perpropionic acid employed.

The content of pyrocatechol in the reaction mixture was 2.3% by weight and the content of hydroquinone was 1.4% by weight, which corresponds to selectivities of 55% for pyrocatechol and 34% for hydroquinone, in each case relative to the perpropionic acid reacted.

The reaction mixture was passed to a distillative working up operation, in the course of which benzene, propionic acid, the excess phenol and the reaction products pyrocatechol and hydroquinone were obtained as pure substances. The phenol thus separated off was recycled, as described above, to the treatment with the ion exchanger and employed again in the reaction.

Example 2

(Comparison example to Example 1)

The procedure followed was as in Example 1, but fresh phenol was added, in the ratio indicated in Example 1, to the unreacted phenol, which had been separated off after the reaction with perpropionic acid and which had not been subjected to a treatment with an ion exchanger and the phenol mixture thus obtained was reacted with perpropionic acid under the same conditions as in Example 1.

In this case, the conversion was 99.3%, relative to the perpropionic acid employed, and the selectivity was 15% for the formation of pyrocatechol and 7% for the formation of hydroquinone, in each case relative to perpropionic acid reacted.

Example 3

200 g of 4-tert.-butylphenol (commercial material) are dissolved in 500 ml of benzene at 40° C. 130 g of a benzene-moist ion exchanger (corresponding to 60 g of dry exchanger) based on sulphonated polystyrene, crosslinked with divinylbenzene, in the H+ form were added, whilst stirring and blanketing with nitrogen, and the mixture was stirred at 40° C. for 30 minutes.

The ion exchanger was then separated off over a glass frit; a solution of 3.8 g of peracetic acid in 50 g of ethyl acetate was slowly added dropwise to 500 g of the solution which was obtained as the filtrate and contained 30% by weight of 4-tert.-butylphenol, whilst stirring and blanketing with nitrogen, the rate of the dropwise addition being adjusted such that the temperature did not rise above 48° C.

After 120 minutes, a peracid conversion of 97.8% of the peracetic acid employed was determined by iodometric titration. According to analysis by gas chromatography, the reaction mixture contained 6.1 g of 4-tert.-butylpyrocatechol, corresponding to a selectivity of 75%, relative to the peracetic acid reacted.

Example 4

(Comparison example to Example 3)

30 g of 4-tert.-butylphenol were dissolved in 80 g of benzene and reacted with 0.8 g of peracetic acid in 9 g of ethyl acetate at 40° C. without the ion exchanger treatment but otherwise under the conditions of Example 3.

After 120 minutes, a conversion of 98.2% of the peracetic acid employed was determined; the content of 4-tert.-butylpyrocatechol was 1.03 g, corresponding to a selectivity of 59% of the peracetic acid reacted.

Example 5

200 g of phenol which had been recovered, by distillation or rectification, as excess phenol from preceding reactions of phenol with perpropionic acid was melted under nitrogen, 30 g of an acid ion exchanger (moisture content 58%) based on a sulphonated styrene/divinylbenzene copolymer (sodium form) were added at 70° C. and the mixture was stirred at 70° C. for 2 hours.

The ion exchanger was then filtered off over a glass frit; a solution of 5 g of perpropionic acid in 17.3 g of a mixture of 83.3% by weight of benzene and 16.7% by weight of propionic acid was slowly added dropwise, at 50° C. and whilst stirring and blanketing with nitrogen, to 150 g of the phenol obtained as the filtrate and the phenol was reacted at 50°-60° C.

After 60 minutes, a conversion of perpropionic acid of 97.4% was determined and the reaction mixture contained 1.9% by weight of pyrocatechol and 1.2% by weight of hydroquinone, corresponding to a selectivity of 55% for the formation of pyrocatechol and 34% for the formation of hydroquinone, in each case relative to perpropionic acid reacted.

Example 6

(Comparison example to Example 5)

Another sample of the feed phenol for Example 5 was reacted without the ion exchanger treatment and under otherwise identical conditions. After a reaction time of 60 minutes, a conversion of 98% of the perpropionic acid employed was determined and the content of pyrocatechol and hydroquinone corresponded to a selectivity of 9% for pyrocatechol and 2% for hydroquinone.

Example 7

200 ml of an acid ion exchanger based on a sulphonated styrene/divinylbenzene copolymer in the H+ form were initially introduced into a heated glass column (diameter 20 mm, length 1,000 mm) and were thermostatically controlled at 65° C. Phenol which originated from the working up of phenol which had already been reacted with less than the equivalent amount of hydrogen peroxide was melted, at 65° C., in a glass vessel which could be heated and was located directly above the glass column packed with the ion exchanger, and was passed over the ion exchanger, from the top downwards, at a rate of 100 ml per hour.

The phenol issuing from the column was collected, under nitrogen. After 1,000 g had passed through the column, a fraction of 95 g was collected and employed in the reaction described below.

0.07 g of perchloric acid (in the form of a 70% strength by weight aqueous solution) and 0.07 g of phosphoric acid (as an 85% strength by weight aqueous solution) were added to the melt at 45° C., whilst stirring and blanketing with nitrogen. A solution of 1.72 g of hydrogen peroxide in 1.7 g of water was then added dropwise in the course of 4 minutes, whereupon the temperature rose to 50° C. The mixture was further blanketed with nitrogen and stirred, whilst being thermostatically controlled at 45° C.

After 300 minutes, a hydrogen peroxide conversion of 96.7% was determined by iodometric titration; the content of pyrocatechol in the reaction mixture was 2.8% by weight (corresponding to 2.75 g) and the content of hydroquinone was 2.0% by weight (corresponding to 1.97 g). These yields correspond to a selectivity of 51% for pyrocatechol and 37% for hydroquinone, in each case relative to the hydrogen peroxide reacted.

Example 8

(Comparison example to Example 7)

94.2 g of the same phenol batch which were employed in the ion exchanger treatment of Example 7 were reacted directly, that is to say without ion exchanger treatment, with 1.6 g of hydrogen peroxide.

After 300 minutes, a hydrogen peroxide conversion of 95.3% was determined, and the selectivities for pyrocatechol and hydroquinone were 28 and 12% respectively, relative to hydrogen peroxide reacted.

Example 9

250 g of p-ethylphenol (commercial material) were melted at 50° C., under nitrogen, and 20 g of a moist weakly acid ion exchanger based on acrylic resin (H+ form), (moisture content: 42%), were added, whilst stirring.

After stirring at 50° C. for 60 minutes, the ion exchanger was separated off over a heated glass suction filter; in a 500 ml glass reaction vessel provided with a stirrer, reflux condenser, thermostatic control, temperature measurement, nitrogen blanketing and dropping device, a solution of 5 g of perisobutyric acid in 45 g of 1,2-dichloropropane was slowly added, whilst stirring and blanketing with nitrogen, to 150 g of the p-ethyl-phenol obtained as the filtrate, at a rate such that the temperature did not rise above 64° C. After a reaction time of one hour at 60° C., a conversion of perisobutyric acid of 98.7% was determined iodometrically; the reaction mixture contained 4.19 g of dihydroxyethylbenzenes, corresponding to a hydroxylation selectivity of 64%.

Example 10

(Comparison example to Example 9)

The 4-ethyl-phenol treated with the ion exchanger in Example 9 was reacted directly, that is to say without ion exchanger treatment, with perisobutyric acid under otherwise identical conditions. After one hour, 260 g of 4-ethylphenol and 5.2 g of perisobutyric acid gave a conversion of perisobutyric acid of over 99%. 3.5 g of dihydroxyethylbenzenes were found in the reaction mixture by analysis by gas chromatography, which corresponds to a hydroxylation selectivity of 51%, relative to the perisobutyric acid employed.

What is claimed is:

1. A process for the preparation of a polyhydric phenol which comprises contacting a phenol containing one or more hydroxyl groups bonded to one or more aromatic nuclei which phenols can contain one or more other substituents in addition to the one or more hydroxyl groups on the aromatic ring which additional substituents are selected from the group consisting of $C_1$ to $C_{10}$ alkyl, $C_3$ to $C_{12}$ cycloalkyl, phenyl, naphthyl, fluorine, chlorine, bromine, nitro, cyano, sulfonic acid, carboxyl, carbo-$C_1$-$C_{10}$ alkoxy, $C_1$-$C_3$ alkoxy, or $C_1$-$C_4$ dialkylamino, it being possible for the alkyl and cycloalkyl radicals to be substituted by fluorine, chlorine, or bromine atoms, or $C_1$-$C_5$ alkoxy, $C_1$-$C_4$ dialkylamino, carboxyl, nitro, cyano, sulfonic acid or $C_1$-$C_{10}$ carbalkoxy groups and for the phenol and naphthyl radicals to be substituted by fluorine, chlorine, bromine, $C_1$-$C_{10}$ alkyl, $C_3$-$C_{12}$ cycloalkyl or nitro, carboxyl, carbo-$C_1$-$C_{10}$ alkoxy, $C_1$-$C_5$ alkoxy, cyano, sulfonic acid or $C_1$-$C_4$ dialkylamino groups with a cation exchanger containing $SO_3-$ and/or $COO-$ groups at a temperature of 0° to 200° C. employing 0.1 to 1000 parts by weight of phenol per hour, separating said phenol from said cation exchanger and thereafter hydroxylating said phenol by contacting the same with a peroxidic hydroxylating agent which contains 1 or more —O—O—groups.

2. A process according to claim 1, wherein the treatment is carried out with a solid ion exchanger based on acrylic acid/divinylbenzene, the $COO^-$ groups being in the acid form or completely or partly in the form of their alkaline earth metal salts and/or alkali metal salts.

3. A process according to claim 1, wherein the phenol to be hydroxylated is an aromatic hydroxy compound which is derived from benzene, naphthalene, phenanthrene or anthracene and has at least one free hydrogen atom on one aromatic nucleus.

4. A process according to claim 3, wherein besides one or more hydroxyl groups, the phenol to be hydroxylated contains no other substituents.

5. Process according to claim 3, wherein in addition to one or more hydroxyl groups on the aromatic nucleus or nuclei, the phenol to be hydroxylated contains, as substituents, one or more identical or different aliphatic, cycloaliphatic, phenyl and/or naphthyl radicals; one or more fluorine, chlorine and/or bromine atoms; one or more $C_1$- to $C_5$-alkoxy, $C_1$- to $C_5$-dialkylamino, carboxyl, nitro, cyano and/or sulphonic acid groups and/or carbalkoxy groups, the alkoxy radicals of which contain 1 to 10 C atoms.

6. Process according to claim 1, wherein molten or dissolved phenol to be hydroxylated is treated with the cation exchanger.

7. Process according to claim 1, wherein the treatment time with the cation exchanger is 1 to 300 minutes.

8. Process according to claim 1, wherein in the case of a discontinuous procedure, 1 part by weight of cation exchanger is used for the treatment of 1 to 1,000 parts by weight of phenol to be hydroxylated, or, in the case of a continuous procedure, 1 part by weight of cation exchanger is brought into contact with 0.1 to 1.000 parts by weight of phenol to be hydroxylated, per hour.

9. A process according to claim 1, wherein the cation exchanger additionally contains basic groups.

10. A process according to claim 9, wherein the basic groups are selected from the group consisting of $NH_2$, NH-alkyl, N-dialkyl, N-alkylhydroxyalkyl, N-diaryl and mixtures thereof, it being possible for these groups to be in the free acid form or completely or partially in the salt form.

11. A process according to claim 1 wherein said peroxidic hydroxylating agent is selected from the group consisting of hydrogen peroxide, a peroxodisulphate, Caro's acid, an alkyl hydroperoxide, an aryl hydroperoxide, a diacyl peroxide, a percarboxylic acid, a percarbonate, a perborate and an adduct of hydrogen peroxide.

12. A process according to claim 1, wherein said phenol is recycled phenol.

13. A process according to claim 1, wherein said phenol has the formula $$R\text{—}\underset{}{\bigcirc}\text{—OH}$$

wherein
R represents hydrogen, $C_1$- to $C_{10}$-alkyl, $C_3$- to $C_{12}$-cycloalkyl, phenyl, naphthyl, fluorine, chlorine, bromine or a nitro, cyano, sulphonic acid, carboxyl, carbo-$C_1$- to $C_{10}$-alkoxy, $C_1$- to $C_3$-alkoxy or $C_1$- to $C_4$-dialkylamino group, it being possible for the alkyl and cycloalkyl radicals to be substituted by fluorine, chlorine or bromine atoms or $C_1$- to $C_5$-alkoxy, $C_1$- to $C_4$-dialkylamino, carboxyl, nitro, cyano, sulphonic acid or $C_1$- to $C_{10}$-carbalkoxy groups and for the phenyl and naphthyl radicals to be substituted by fluorine, chlorine, bromine, $C_1$- to $C_{10}$-alkyl, $C_3$- to $C_{12}$-cycloalkyl or nitro, carboxyl, carbo-$C_1$- to $C_{10}$-alkoxy, $C_1$ to $C_5$-alkoxy, cyano, sulphonic acid or $C_1$- to $C_4$-dialkylamino groups.

14. A process according to claim 1, wherein said phenol is one of the formula

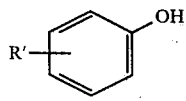 (II)

wherein
R' represents hydrogen, $C_1$- to $C_3$-alkyl, $C_5$- to $C_7$-cycloalkyl, phenyl, fluorine, chlorine or a nitro, sulphonic acid, carbohydroxy, carbo-$C_1$- to $C_3$-alkoxy, $C_1$- to $C_2$-alkoxy or $C_1$- to $C_2$-dialkylamino group.

15. A process according to claim 1, wherein said phenol is a monohydric phenol of the formula

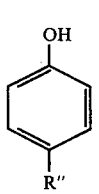 (III)

wherein
R" denotes hydrogen, $C_1$- to $C_5$-alkyl, $C_5$- to $C_7$-cycloalkyl, phenol, fluorine, chlorine, or a nitro, sulphonic acid, carbohydroxy, carbo-$C_1$- to $C_4$-alkoxy, $C_1$- to $C_3$-alkoxy or $C_1$- to $C_2$-dialkylamino group.

* * * * *